United States Patent [19]

Shimizu et al.

[11] Patent Number: 5,139,938
[45] Date of Patent: Aug. 18, 1992

[54] PRODUCTION OF SUBSTANCES WITH AN ACETIC ACID-PRODUCING AND ASSIMILATING BACTERIUM INHIBITED BY ACETIC ACID

[75] Inventors: Norio Shimizu, Kokubunji; Shinichi Fukuzono, Hachioji; Kiyoshi Fujimori, Tokyo; Nobuko Nishimura, Katsuta; Yoji Odawara, Kokubunji, all of Japan

[73] Assignee: Hitachi, Ltd., Tokyo, Japan

[21] Appl. No.: 157,719

[22] Filed: Feb. 19, 1988

[30] Foreign Application Priority Data

Mar. 23, 1987 [JP] Japan .................. 62-65710

[51] Int. Cl.$^5$ .................. C12P 21/00; C12P 7/54; C12N 15/52; C12N 9/38
[52] U.S. Cl. .................. 435/69.8; 435/69.1; 435/71.1; 435/140; 435/172.3; 435/207; 435/252.33; 435/849; 935/22; 935/23; 935/60; 935/73
[58] Field of Search .................. 435/69.1, 69.2, 69.8, 435/140, 172.3, 783, 207, 252.33, 849; 935/92, 23, 60, 73

[56] References Cited

U.S. PATENT DOCUMENTS 4,654,215 3/1987 Yamada et al. .................. 435/140 X

FOREIGN PATENT DOCUMENTS

| 0165613 | 12/1985 | European Pat. Off. |
| 0196061 | 10/1986 | European Pat. Off. |
| 0219791 | 4/1987 | European Pat. Off. |
| 53-29985 | 3/1978 | Japan |
| 57-36983 | 2/1982 | Japan |
| 58-78584 | 12/1983 | Japan |

OTHER PUBLICATIONS

Analytica Chimica Acta, vol. 190, 1986; pp. 195-203, Elsevier Science Publishers B. V., Amsterdam, NL; J. Moller et al.: "On-Line High-Performance Liquid Chromatography for Monitoring Fermentation Processes for Penicillin Production".
Patent Abstracts of Japan, vol. 2, No. 72, 31 May 1978, p. 838 C 7 & JP-A-53 29 985 (Kanegafuchi Kagaku Kogyo K.K.) Mar. 20, 1978.

*Primary Examiner*—David M. Naff
*Attorney, Agent, or Firm*—Antonelli, Terry Stout & Kraus

[57] ABSTRACT

Cultivation of microorganisms or animal cells or plant cells is carried out to produce high density cultivation, high cell yield and high production of desired metabolite products by monitoring acetate concentration in culture broth and regulating assimilation of acetate in the culture broth by the microorganisms or animal cells or plant cells to control the acetate concentration to a set value or less. Preferably, an acetic acid-producing bacterium that is inhibited by acetic acid and is capable of assimilating acetic acid is cultured to produce biologically active substances such as enzymes. The bacterium may be a recombinant *Escherichia coli* and an inducer which acts on a promoter in an expression vector is added to produce the desired metabolite product. The inducer is 3-β-indolylacrylic acid when the promoter is trp-promoter or isopropyl-β-D-thiogalactoside when the promoter is lac-promoter or tacpromoter.

15 Claims, 9 Drawing Sheets

CULTURE TIME (h)

CULTURE TIME (h)

EXCHANGE OF MEDIUM FOR SUBSTRATE FEEDING

CULTURE TIME (h)

PRODUCTION OF SUBSTANCES WITH AN ACETIC ACID-PRODUCING AND ASSIMILATING BACTERIUM INHIBITED BY ACETIC ACID

BACKGROUND OF THE INVENTION

1. Field of the Invention

The present invention relates to a method for cultivation of microorganisms or animal cells or plant cells, in particular, recombinant microorganisms with acetate concentration monitoring to efficiently produce desired useful substances such as enzymes or biologically active substances. The present invention also relates to an apparatus for the method.

2. Prior Art Statement

By cultivation of microorganisms or animal cells or plant cells, especially recombinant microorganisms, there has been hitherto produced enzymes, antibiotics, amino acids, or biologically active substances such as hormones or the like which are metabolites. This method for cultivation is mostly batch culture which comprises simply charging medium and seed cells in a culture tank. As a matter of course, the productivity is low.

In order to enhance the productivity, there is performed a culture method in which a substrate or inducer is added during the course of cultivation. However, it is a problem that at which point of the cultivation the substrate or inducer should be added and its clear indicator is unknown. On the other hand, in cultivation using baker's yeast, there is known a method which comprises detecting the production of ethanol with respiratory quatient and feeding substrate [Japanese Patent KOKAI (Laid-Open) Nos. 36983/1982 and 78584/1983]. However, this is cultivation for producing cell mass per se which are quite dissimilar to producing the metabolites.

Further in spite of adding substrate, there is a phenomenon that the growth rate of cells decreases during cultivation. This is said to be due to proliferation-inhibitory substances accumulated in culture broth. However, there is little finding on the proliferation-inhibitory substances. Also from this aspect, efficient cultivation can be achieved only with difficulty. In order to remove the proliferation-inhibitory substances without specifying them, there is known a method which comprises withdrawing culture broth intermittently or continuously, recovering the cells by centrifugation and charging the cells again in a culture tank [Japanese Patent KOKAI (Laid-Open) No. 29985/1978]. However, this method is directed to baker's yeast and mass production of cells per se, not a process for allowing the cells to produce the desired substances.

The prior art described above was developed without consideration of adding substrate or the like or monitoring proliferation-inhibitory substances and involved problems of difficulty in cell growth and production of metabolites.

SUMMARY OF THE INVENTION

An object of the present invention is to provide a method for cultivation of microorganisms or animal cells or plant cells, especially recombinant microorganisms with acetate concentration monitoring to produce the metabolites as well as an apparatus for the method.

A first invention of the present invention relates to a method for cultivation of microorganisms or animal cells or plant cells to produce the metabolites which comprises a step of monitoring acetate concentration in culture broth and controlling the acetate concentration to a set value or less through regulating assimilation of the acetate in culture broth by the microorganisms or animal cells or plant cells.

Further a second invention of the present invention relates to a cultivation apparatus comprising a culture tank for performing cultivation, an acetate concentration analyzer in culture broth, a substrate tank for storing substrate, a substrate feeding device of variable flow type for feeding substrate and a control device for outputting a signal for controlling a substrate flow from the substrate feeding device based on a signal from the analyzer.

DETAILED DESCRIPTION OF THE PREFERRED EMBODIMENTS

Hereafter, the present invention is concretely described below with the method for cultivation of *Escherichia coli* strain HB 101 [PTREZ 1], which was deposited with FRI under the Budapest Treaty and given Accession No. FERM BP-815, bearing hybrid plasmid pTREZ 1 comprising trp (tryptophane)-promoter and $\beta$-gal ($\beta$-galactosidase) gene ligated therewith, and an apparatus for the method. However, the present invention is not deemed to be limited thereto.

The trp-promoter portion of hybrid plasmid pTREZ 1 is a DNA fragment of about 500 bp (base pairs) containing trp promoter-operator of *Escherichia coli*, trp-L (leader peptide gene) and a part of the tip of trp-E (anthranilate synthetase), which is inserted in EcoR I site of pBR 322 plasmid. On the other hand, $\beta$-gal gene has a size of 6.2 kb excised from pMC 1403 [J. Bacteriol., 143, 971–980 (1980)] and is inserted between EcoR I site of trip-promoter and Sal I site of pBR 322. As such, $\beta$-gal gene of hybrid plasmid pTREZ 1 is under control of trip-promoter.

It is known that by adding 3-$\beta$-indolylacrylic acid (hereafter simply referred to as IA) during cultivation, a hydrid plasmid containing trp-promoter causes expression of gene [(Nature, 291, 503–506 (1981)]. This is due to inactivation of repressor for controlling transcription of gene with IA.

As a result of various investigations on a method of cultivation for efficiently producing β-gal using recombinant *Escherichia coli* capable of producing β-gal as a model, the present inventors have succeeded in efficient proliferation of cells and efficiently production of desired substances and, have come to accomplish the present invention.

Figure 2A:
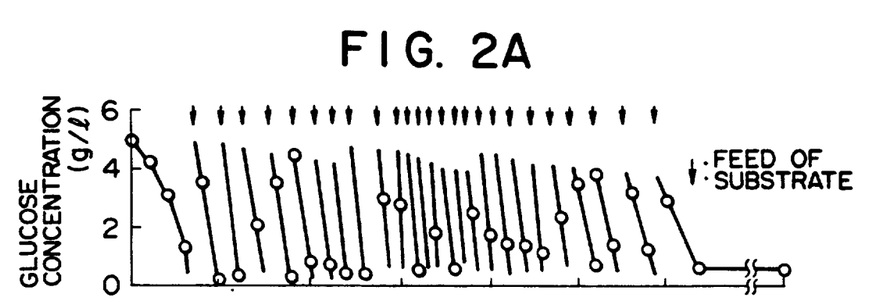
FIGS. 2A-2C are graphs showing results of fed-batch culture using recombinant *Escherichia coli*.
Figure 2B:
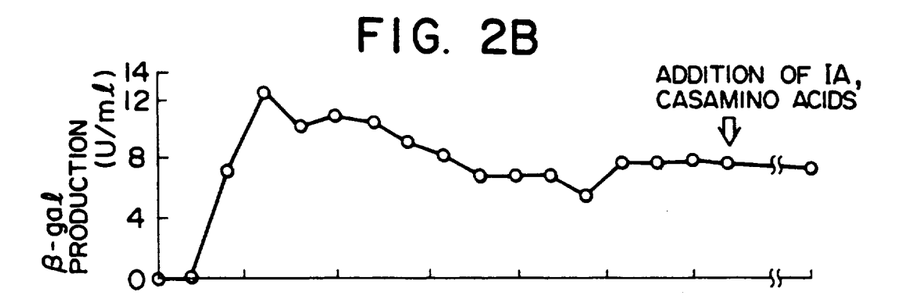
Figure 2C:
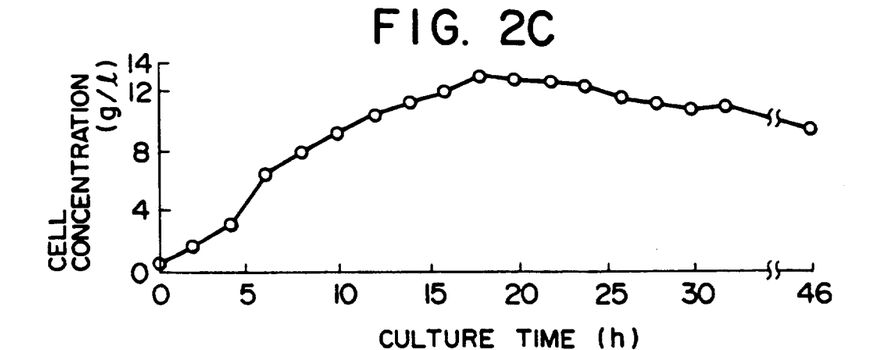

FIGS. 2A-2C show the results of fed-batch culture using recombinant *Escherichia coli*. Namely, FIGS. 2A-2C are graphs showing an example of results of fed-batch culture in relationship between culture time (h, abscissa) and cell concentration (g/l), amount of β-gal (U/ml) and glucose concentration (g/l) [ordinate].

Cultivation was performed by feeding glucose and casamino acid medium with monitoring a rise in dissolved oxygen concentration. The cell concentration reached 13 g/l at 18 hours of cultivation but at this time, the cell growth stopped. For inducion of β-gal production, IA as an inducer and casamino acids as nutrients, i.e., substrate were added at 32 hours of cultivation but β-gal production was not induced. The reason why the cell growth stopped and no β-gal production was induced as such seemed to be due to the presence, in culture supernatant, of substances which inhibit cell growth or β-gal production.

Figure 3:
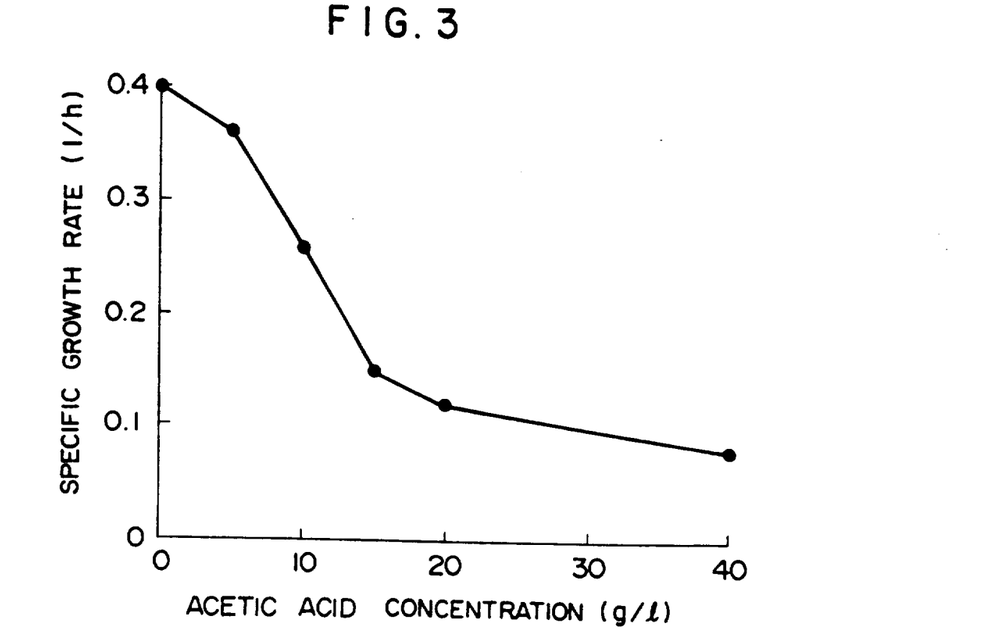
FIG. 3 is graphs showing an example of relationship between acetic acid concentration in culture broth and specific growth rate.
Figure 4:
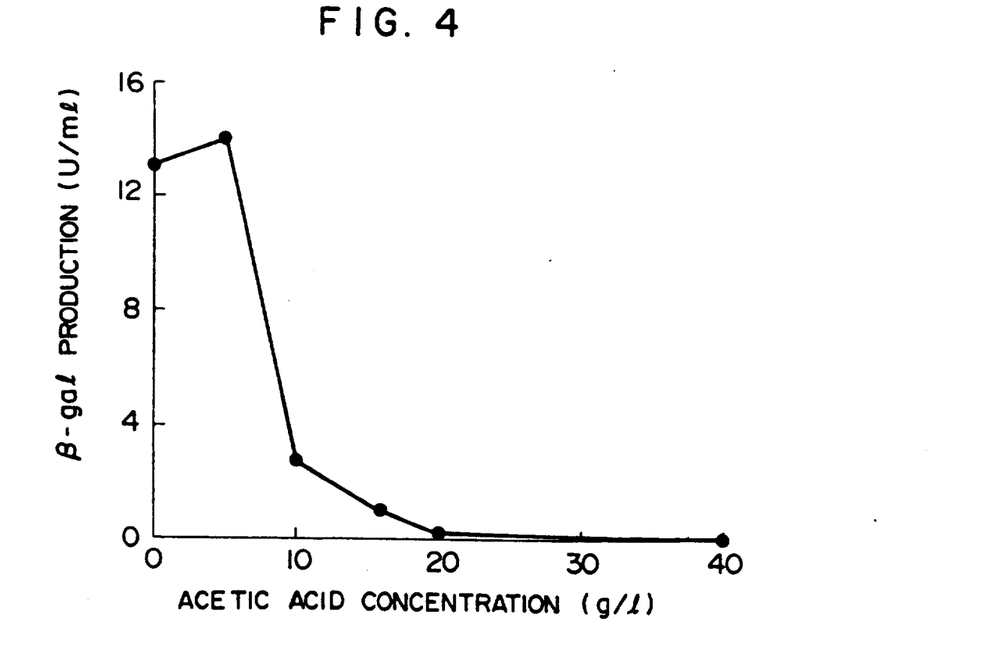
FIG. 4 is a graph showing an example of relationship between acetic acid concentration and $\beta$-gal production.

Thus, the supernatant of culture broth at 19 hours when cell growth stopped was collected and cell growth-inhibitory substances were separated from the supernatant using ultrafiltration membrane and ion-exchange resin. The thus separated liquid was analyzed for organic acids using an isotachophoretic analyzer. The results reveal that acetic acid was accumulated in a high concentration of 33 g/l. In culture broth, acetic acid is generally present in the form of acetate owing to pH-adjustment. Therefore, the corresponding amount of acetate was added to fresh medium followed by cultivation, whereby the cell growth was inhibited (cf. FIG. 3). From this fact, it was found that a substance participating in the cell growth inhibition was acetate. With regard to expression of gene (β-gal production), almost the same results as in the cell growth inhibition were obtained (cf. FIG. 4). That is, FIG. 3 is a graph showing an example of the relationship between an acetic acid concentration (g/l, abscissa) in culture broth of recombinant *Escherichia coli* and its specific growth rate (1/h, ordinate) and FIG. 4 is a graph showing an example of the relationship between an acetic acid concentration (g/l abscissa) in culture broth and β-gal production (U/ml, ordinate).

It was also confirmed by analysis of the supernatant of culture broth using gas chromatography that the inhibitory substance was acetate.

Figure 5:
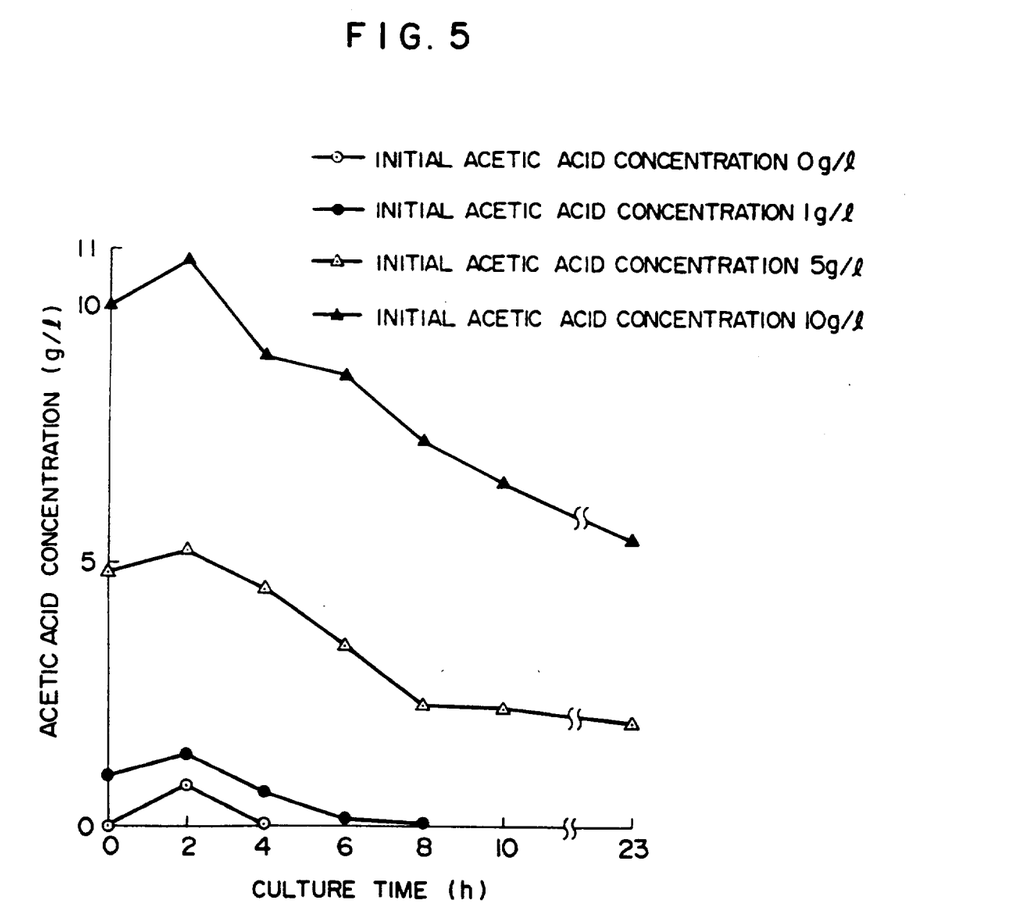
FIG. 5 is graphs showing an example of acetic acid assimilation of recombinant *Escherichia coli*.
Figure 6:
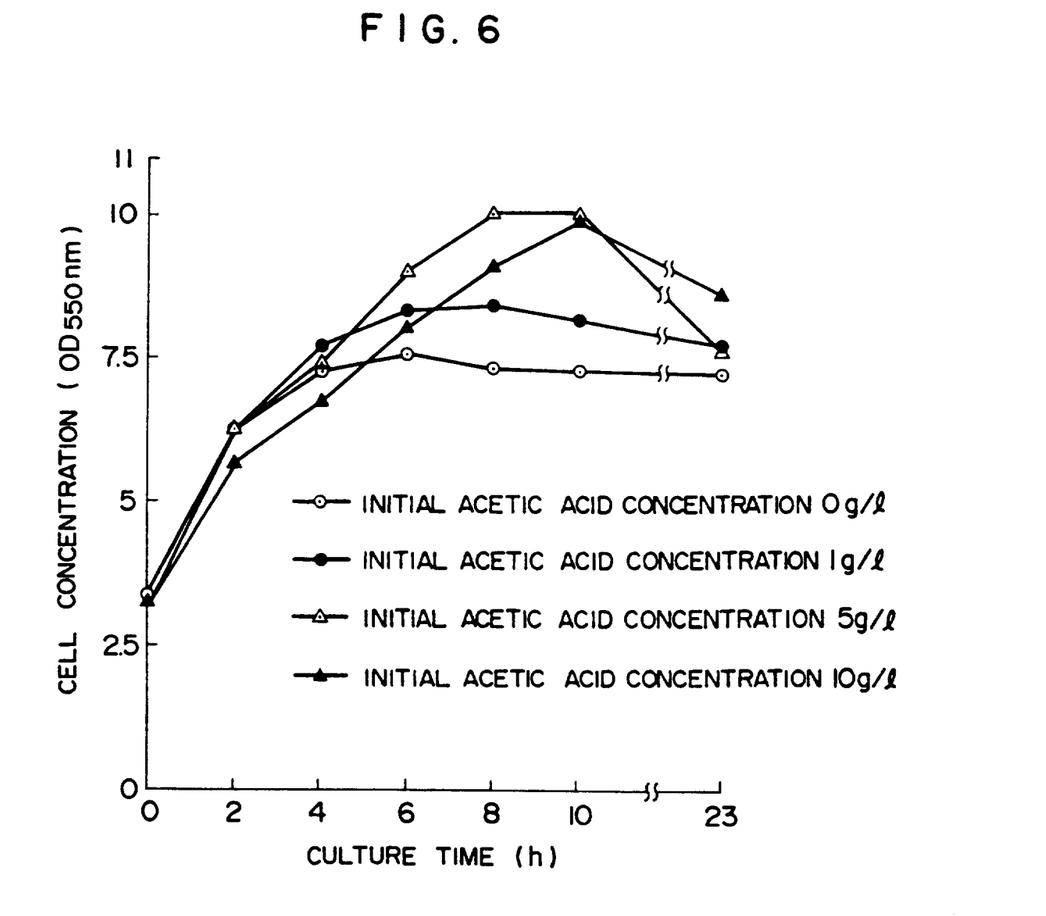
FIG. 6 is graphs showing cell growth in relationship between culture time and cell concentration under the respective conditions of FIG. 5.
Figure 7A:
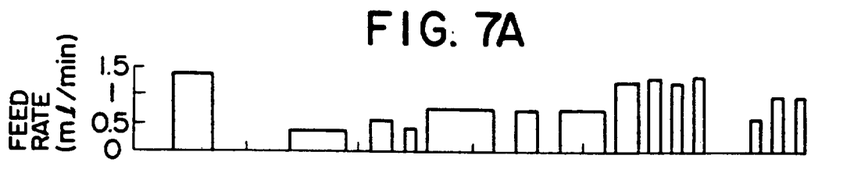
FIGS. 7A-7D, 8A-8D and 9A-9D are graphs showing examples of results of fed-batch culture using recombinant *Escherichia coli*, with acetic acid concentration monitoring in accordance with the present invention.
Figure 7B:
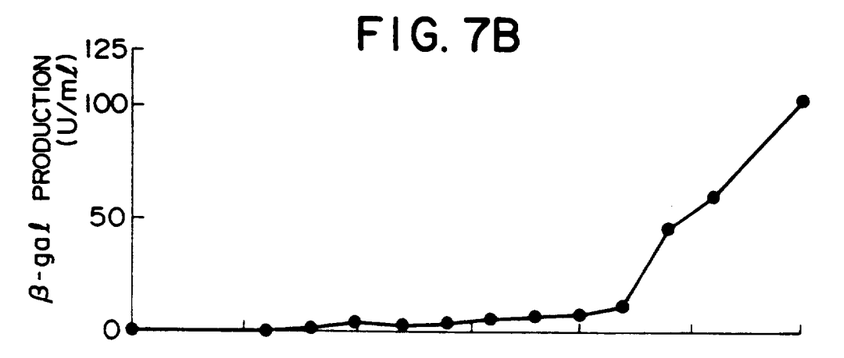
Figure 7C:
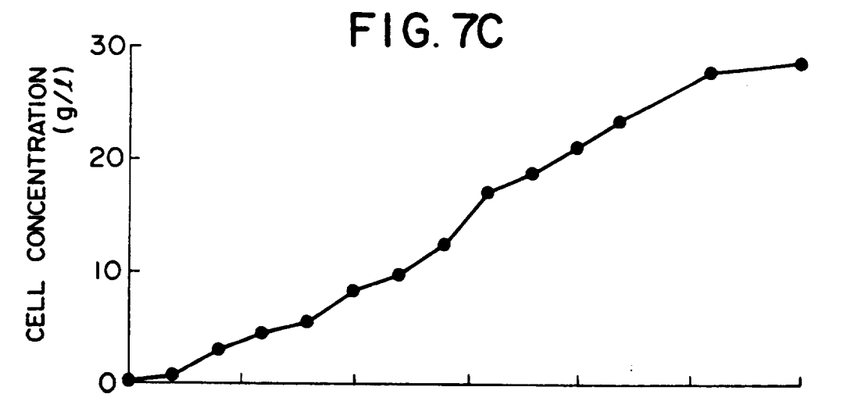
Figure 7D:
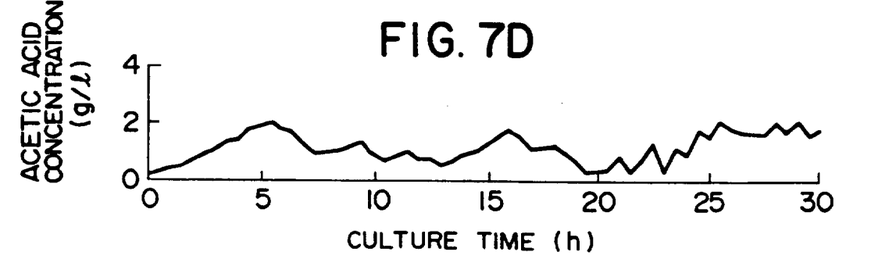
Figure 8A:
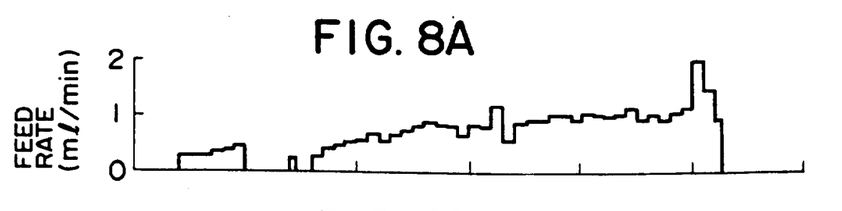
Figure 8B:
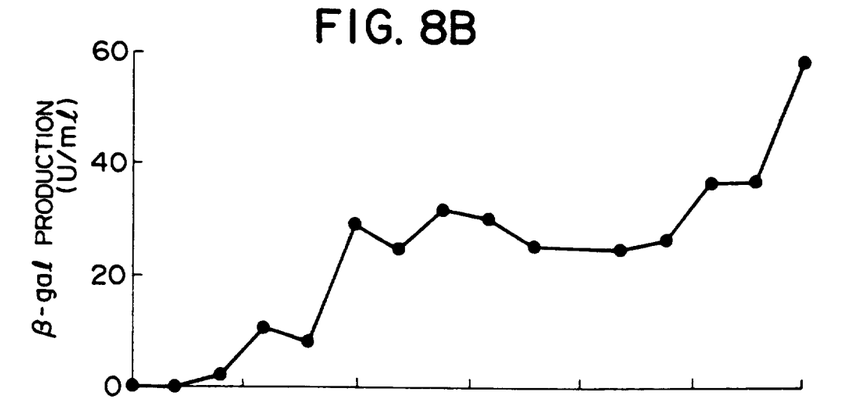
Figure 8C:
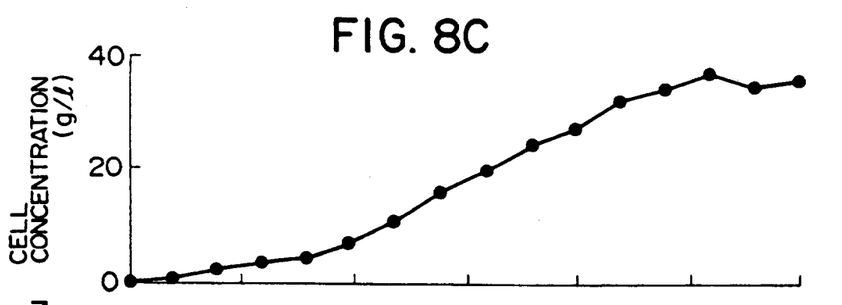
Figure 8D:
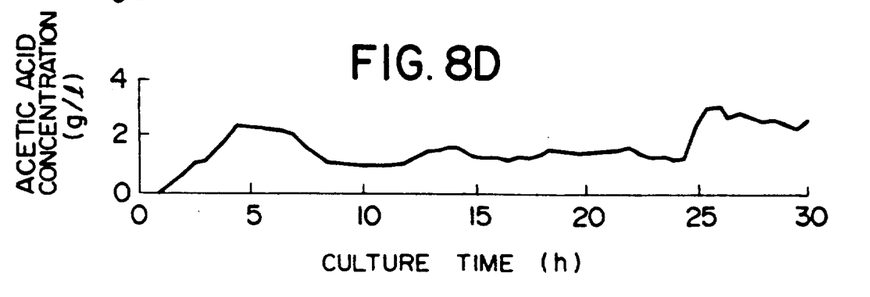
Figure 9A:
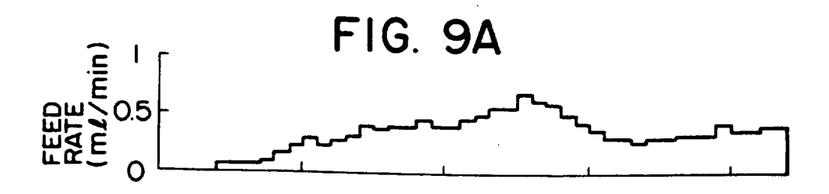
Figure 9B:
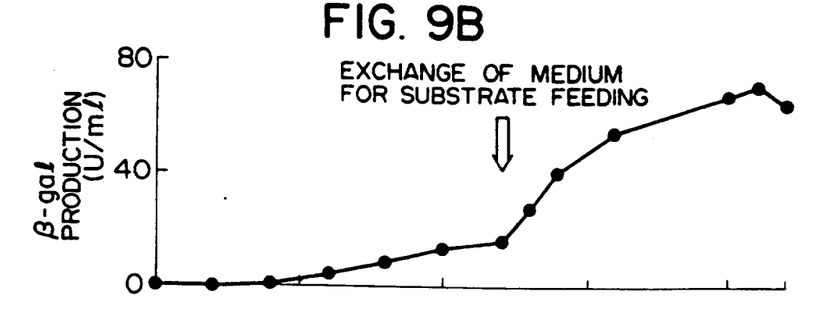
Figure 9C:
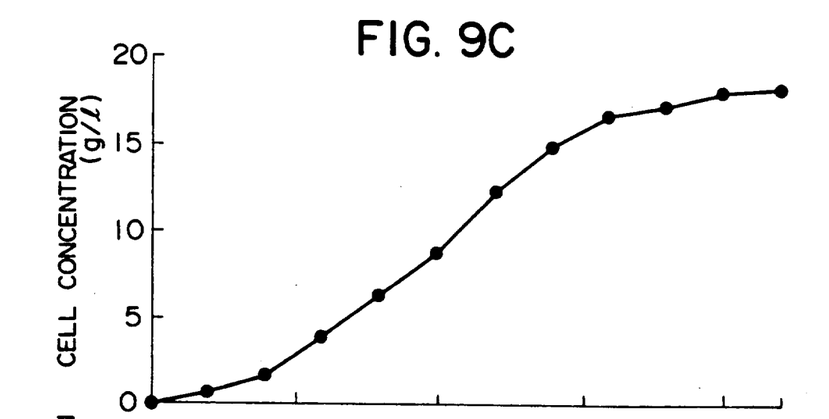
Figure 9D:
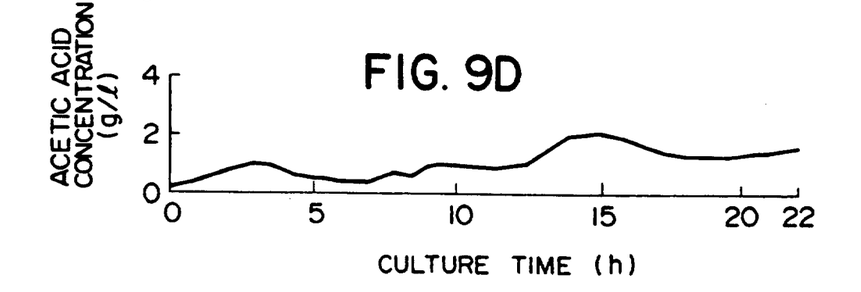
Figure 10A:
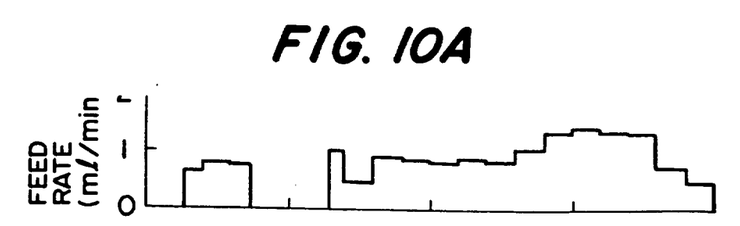
FIGS. 10A-10D are graphs showing results of cultivation in a Comparative Example.
Figure 10B:
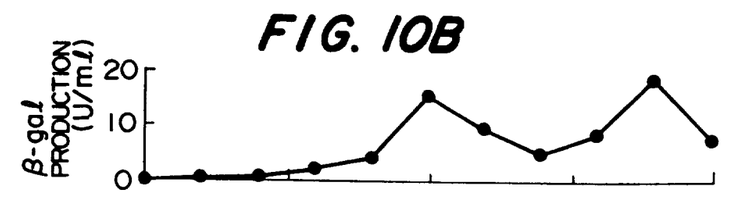
Figure 10C:
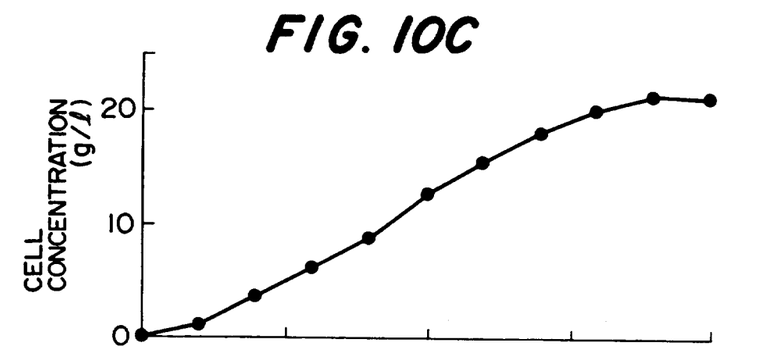
Figure 10D:
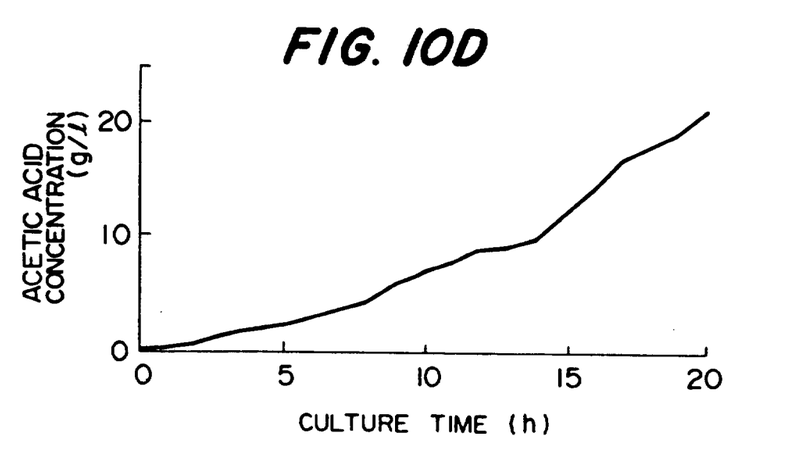

As described above, the acetate accumulated in culture broth inhibits the cell growth and based on this finding, the present inventors have come to conceive that by feeding a substrate with acetate concentration monitoring, the cells could be efficiently proliferated. For such a purpose, it is necessary to remove the acetate accumulated in culture broth. In order to remove the acetate, the present inventors performed removal of acetate by allowing the cells to assimilate the acetate. Thus, acetate was added to culture broth in 0 to 10 g/l calculated as an acetic acid concentration and investigations were made on a possibility of acetate assimilation of recombinant bacteria. As shown in FIG. 5, an acetic acid concentration in culture broth increased at the initial stage of cultivation because 1 g/l of glucose was added to culture broth but the acetic acid concentration gradually decreased thereafter. This reveals that the acetate in culture broth was assimilated by the cells. Changes dependent on time of cell concentration are shown in FIG. 6. Namely, FIG. 5 is graphs showing an example of acetate assimilation of recombinant *Escherichia coli* in relationship between incubation time (h, abscissa) and acetic acid concentration (g/l, ordinate). In Figure, initial acetic acid concentrations of 0, 1, 5 and 10 g/l are shown by "-○-", "-●-", "-△-" and "-▲-", respectively. FIG. 6 is graphs showing cell growth in relationship between incubation time (h, abscissa) and cell concentration (QD. 550 nm, ordinate) under each condition of FIG. 5. As is clearly seen from FIG. 6, the cell concentration increased by acetate assimilation of the cells, as compared to the case that no acetate was added.

These results indicate that it is convenient, effective and advantageous to control the assimilation of acetate, i.e., acetate concentration, by controlling an amount of substrate fed.

Based on the foregoing results, it has been found that advantageous is a method for cultivation in which, by monitoring acetate concentration in culture broth and when the acetate concentration becomes higher than a set value, an amount of fed substrate is reduced or feeding of substrate is discontinued thereby allowing the cells to assimilate acetate to reduce the acetate concentration and at the point of time when the acetate concentration becomes lower than the set value, substrate is again fed.

From the results of FIG. 3, it is noted that the acetate concentration in culture broth in the present invention be suppressed to 15 g/l or less, preferably 5 g/l or less. For the set value to control the feeding of substrate, not only the acetate concentration is set at 5 g/l but also it is possible to set ranges, for example, from 1 to 3 g/l.

In addition, acetate concentration in culture broth exhibited inhibition on expressior of gene, also upon the addition of an inducer thereby to cause expression of gene (FIG. 4), likewise the case of cell growth. From these results, it is desired that also in the case of gene expression, the acetate concentration be 15 g/l or less, particularly 5 g/l.

In the present invention, the acetate can be detected rapidly and accurately by introducing the supernatant of culture broth into an isotachophoretic analyzer, a gas chromatograph, a liquid chromatograph, a mass spectrometer, etc.

As the cells usable in the present invention, there are, for example, microorganisms such as yeast, *Bacillus subtilis* and *Actinomyces;* animal cells; plant cells; or recombinant cells of these microorganisms and animal cells or plant cells, etc., growth of which is inhibited by acetic acid, in addition to recombinant *Escherichia coli* described above. The present invention is applicable to these cells as far as the cells have an ability of assimilating the acetate.

Substrate which is fed to control the assimilation of acetate with microorganisms or animal cells or plant cells is generally nutrients and include casamino acid which is a mixture of amino acids, amino acids, glucose, yeast extract, etc.

Further for inducing the production of desired products such as enzymes, biologically active substances and so on, when the cells are recombinant *Escherichia coli*, cultivation in medium containing no tryptophan that suppresses expression of gene or having a low tryptophan concentration is effective in the case of trp promoter; in the case of lac-promoter and tac-promoter, addition of IPTG (isopropyl-β-D-thiogalactoside) or the like is effective; and, in the case of $P_L$-promoter, elevation of the temperature of cultivation is effective. These inducers or induction conditions are also applicable to recombinant microorganisms other than *Escherichia coli*. As the nutrients added for induction of the production of desired products, casamino acid which is a mixture of amino acids, amino acids, glucose, yeast extract, etc. are effective.

In the cultivation apparatus of the present invention, as has already been described briefly, a sample preparation device may be provided before the acetate concentration analyzer to prepare the collected culture broth sample in a form suited for the analyzer, but this is not necessarily required.

A preferred example of a device for feeding substrate is a pump.

As a matter of course, conduits for connecting each of these devices, facilitates for supplying raw materials and the like may additionally be attached to the apparatus.

The present invention will be described in more detail with reference to the examples below but is not deemed to be limited thereto.

EXAMPLE 1

Figure 1:
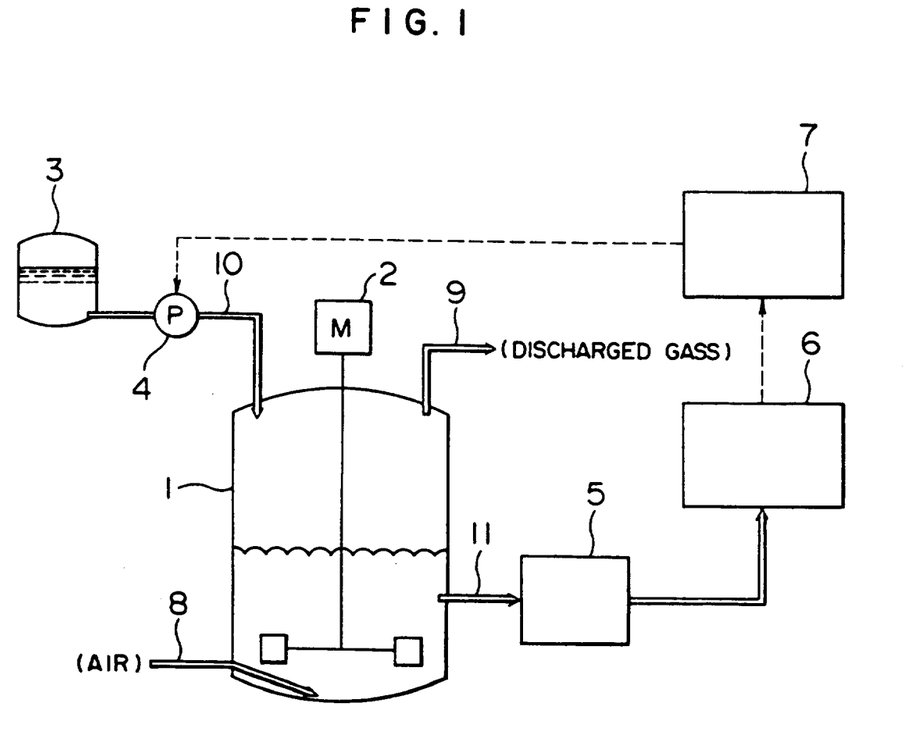
FIG. 1 is a schematic illustration of an example of cultivation apparatus of the present invention.

An example of the cultivation apparatus of the present invention is schematically illustrated in FIG. 1.

In FIG. 1, numeral 1 denotes a culture tank, 2 denotes a stirrer, 3 denotes a substrate tank, 4 denotes a pump for feeding substrate, 5 denotes a sample preparation device, 6 denotes an acetate concentration analyzer, 7 denotes a computer for control and, 8 to 11 denote conduits.

In the culture tank 1 charged with culture broth containing medium and microorganisms, a stirring part of the stirrer 2 equipped with motor M is encased. The air introducing conduit 8 is connected with the culture tank 1 at the bottom thereof. Exit gas discharging conduit 9 is connected with the culture tank 1 at the upper part thereof. Culture broth withdrawing conduit 11 is connected with the culture tank 1 at the side thereof so as to contact with the culture broth. The sample preparation device 5 is connected with the acetate concentration analyzer 6 via the conduit 11. Substrate feeding pump 4 of variable flow type is connected with the substrate tank via substrate feeding conduit 10 at the upper part of the culture tank 1. The control computer 7 is connected with the acetate concentration analyzer 6 and the substrate feeding pump 4.

In the sample preparation device 5, a cell separator and a device for acidifying the sample solution are encased. In the acetate concentration analyzer 6, a mass spectrometer or a gas chromatography and so on are encased.

Hereafter the operation of the present invention is in the culture tank 1, microorganism and substrate supplied from the substrate tank 3 as well as air from the conduit 8 are agitated by the stirrer 2, whereby microorganisms grow. The culture broth is withdrawn through the conduit 11 and sent to the sample preparation device 5, where cells are removed and at the same time the sample is acidified with an acid so that the acetate in the sample is converted into acetic acid. Then the sample is introduced into the acetate concentration analyzer 6. In case that a gas chromatograph is encased in the acetate concentration analyzer 6, the sample is used as it is in an acidic solution state and however, in case that a mass spectrometer is encased, acetic acid vaporized by bubbling with air is provided for analysis. A value of acetate concentration in culture broth analyzed with the acetate concentration analyzer 6 is transferred to the control computer and compared with the set value. In case that the determined acetate concentration is higher than the set value, a signal is sent to the substrate feeding pump 4 so as to stop the feeding of substrate or retard a substrate feeding rate, whereby an amount of feeding substrate is controlled. On the other hand, when the acetate concentration is lower than the set value, a signal is sent to the substrate feeding pump 4 so as to initiate the feeding of substrate or increase the substrate feeding rate, whereby an amount of feeding substrate is controlled. Thus, the acetate concentration in culture broth can be controlled to the set value or lower and the growth rate of cells can be maintained on a high level.

EXAMPLE 2

Acetate in the cell culture broth was monitored with a gas chromatograph and a substrate-feeding amount was controlled so that acetate concentration in culture broth became 2 g/l or less. In order to suppress the action of trp-promoter upon cell growth, tryptophan was added to medium.

*Cells:* E. coli strain HB 101 [PTREZ 1] having hybrid plasmid pTREZ 1.

*Initial medium:* M9-casamino acid medium; which was composed of 1 g of $NH_4Cl$, 6 g of $Na_2HPO_4$, 3 g of $KH_2PO_4$, 0.5 g of NaCl, 0.1 g of $MgSO_4 \cdot 7H_2O$, 15 mg of $CaCl_2 \cdot 2H_2O$, 0.1 g of thiamine hydrochloride, 0.1 g of proline, 0.01 g of tryptophan, 5 g of glucose, 2.5 g of casaminc acid, 1.5 g of yeast extract and 1 liter of distilled water, and had a pH of 7.0. To the medium was added 50 mg/liter of ampicillin (Ap) in order to grow only *E. coli* having hydrid plasmid.

Medium for substrate feeding: This medium was composed of 200 g of glucose, 4 g of proline, 100 g of casamino acid, 60 g of yeast extract, 0.4 g of tryptophan and 1 liter of distilled water, and had a pH of 7.0.

Culture conditions: *E. coli* having hybrid plasmid was inoculated into four 500 ml shaker flasks each containing 50 ml of M9-casamino acid medium and followed by cultivation overnight by means of a shaker under the conditions of a stroke of 7 cm, an oscillation of 115 times/min. at 37° C. Into a 5 liter jar fermenter containing M9-casamino acid medium was inoculated 200 ml of the seed culture thus obtained. Culture was initiated at an initial liquid volume of culture broth of 2 liters, at 37° C. and pH 7.0 at gas flow rate of 2 liters/min. Acetate concentration in culture broth was measured by introducing the supernatant into a gas chromatograph packed with PEG 600 + Fulsin P (manufactured by Gasukuro kogyo). At the point when acetate concentration reached 2 g/l feeding of substrate was discontinued.

Results: The results are shown in FIGS. 7A–7D.

That is to say, FIGS. 7A–7D are graphs showing an example of cultivation in accordance with the present invention in relationship between culture time (h, abscissa) and acetic acid concentration (g/l), cell concentration (g/l), amount of β-gal produce (U/ml) and feeding rate (ml/min) [ordinate].

As shown in FIGS. 7A–7D, acetate was produced by feeding substrate but when the feeding of substrate was discontinued, acetate is assimilated by the cells, whereby acetate concentration in the culture broth decreased. By conducting cultivation on a suppressed level of the acetate concentration in culture broth, the cell concentration reached a high value of 29 g/l at 30 hours of cultivation. In order to suppress the action of trp-promoter, tryptophan was added to the medium for feeding substrate so that β-gal production could be suppressed until 22 hours of cultivation. However, 22 hours after, the suppression was derepressed due to a reduced concentration of tryptophan so that β-gal produced finally reached 104 U/ml. In this example, β-gal was produced because the suppression was released due to the reduced tryptophan concentration, though the β-gal production can be initiated also by the addition of IA as an inducer. As described above, the cell concentration reached a high level of 29 g/l by lowering the acetate concentration in culture broth and the cell yield could be maintained at a high level of 0.57 g·cells/g·glucose.

EXAMPLE 3

Acetate in the cell culture broth was monitored with a gas chromatograph and a substrate-feeding amount was controlled so that acetate concentration in culture broth become 2 g/l or less. No tryptophan was added to medium and β-gal was produced in association with cell growth.

Fed-batch culture was performed using the same strain under the same culture conditions as in Example 2 except for using tryptophan-free medium.

Results: An example of cultivation results is shown in FIGS. 8A–8D in a relationship similar to FIGS. 7A–7D.

As shown in FIGS. 8A–8D, β-gal was produced in association with the cell growth. The cell concentration reached a high level of 36 g/l at 30 hours of cultivation and the cell yield was 0.54 g.cells/g.glucose. However, β-gal production in this case was 59 U/ml which was lower than the value in Example 1.

EXAMPLE 4

Acetate in cell culture broth was monitored with a gas chromatograph and a substrate-feeding amount was controlled so that acetate concentration in culture broth became 2 g/l or less. At the early stage of cultivation, tryptophan was added to medium for feeding substrate thereby to suppress β-gal production. At the late stage of cultivation, β-gal production was performed using tryptophan-free medium for feeding substrate.

The initial medium and medium for feeding substrate used in the early stage of cultivation were those similar to Example 1. At the late stage of cultivation, however, there was used medium for feeding substrate obtained by omitting yeast extract and tryptophan from the medium for feeding substrate of Example 1. Fed-bath culture was performed using the same strain under the same culture conditions as in Example 2 except for the medium described above.

Results: An example of cultivation results is shown in FIGS. 9A–9D in a relationship similar to FIGS. 7A–7D.

As shown in FIGS. 9A–9D, feeding was initiated at 12 hours of cultivation using tryptophan-free medium for feeding substrate and β-gal production was suddenly initiated and the maximum 70 U/ml of β-gal was produced. The cell concentration was 18.6 g/l and the cell yield was 0.52 g·cells/g·glucose.

COMPARATIVE EXAMPLE 1

Any means for suppressing the formation of acetate was not taken except that substrate was fed as in Examples 2 and 3 so that glucose concentration in culture broth was at a low concentration of 1 g/l or less.

Fed-batch culture was performed using the same strain under the same culture conditions as in Example 2.

Results: An example of cultivation results is shown in FIGS. 10A–10D in a relationship similar to FIGS. 7A–7D.

As shown in FIGS. 10A–10D, acetate was formed in association with cell growth. At 20 hours of cultivation when acetate concentration reached 21 g/l the cell growth stopped. At this time, the cell concentration was 21 g/l but the cell yield was at a low level of 0.36 g·cells/g·glucose, indicating a very poor productivity. Further β-gal production was as extremely low as 8 U/ml.

As described above, according to the present invention, the acetate concentration in culture broth can be reduced so that there can be exhibited remarkable effects of easily achieving high density cultivation, high cell yield and high production of desired products. For example, in the case of β-gal production, high density cultivation of more than 25 g/l high cell yield of more than 0.5 g.cells/g.glucose and high production of β-gal of more than 50 U/ml can be achieved.

While the invention has been described in detail and with reference to specific embodiments thereof, it will be apparent to one skilled in the art that various changes and modifications can be made therein without departing from the spirit and scope thereof.

What is claimed is:

1. A method of producing a metabolite other than acetic acid by cultivation of an acetic acid-producing bacterium that is inhibited by acetic acid and is capable of assimilating acetic acid comprising,
   feeding a nutrient substrate to a culture broth and culturing said bacterium in the culture broth whereby acetic acid as acetate and said metabolite are produced.
   monitoring acetate concentration in the broth during said culturing,
   controlling the acetate concentration in the broth below a set value by reducing or discontinuing feeding of the nutrient substrate when the acetate concentration becomes higher than said set value to allow the bacterium to assimilate the acetate to decrease the acetate concentration in the broth and by increasing or again feeding nutrient substrate when the acetate concentration becomes lower than said set value, and
   recovering said metabolite.

2. A method for producing a metabolite according to claim 1, wherein said set value of acetate concentration is not greater than 15 g/l.

3. A method for producing a metabolite according to claim 1, wherein said nutrient substrate is at least one selected from the group consisting of an amino acid, glucose and yeast extract.

4. A method for producing a metabolite according to claim 1, wherein said metabolite is a biologically active substance.

5. A method for producing a metabolite according to claim 1, wherein said metabolite is an enzyme.

6. A method for producing a metabolite other than acetic acid by cultivation of an acetic acid-producing recombinant bacterium that is inhibited by acetic acid and is capable of assimilating acetic acid comprising, feeding a nutrient substrate to a culture broth and culturing said bacterium in the culture broth whereby acetic acid as acetate and said metabolite are produced, monitoring acetate concentration in the broth during said culturing, controlling the acetate concentration in the broth below a set value that it is not greater than 15 g/l by reducing or discontinuing feeding of the nutrient substrate when the acetate concentration becomes higher than said set value to allow the bacterium to assimilate the acetate to decrease the acetate concentration in the broth and by increasing or again feeding nutrient substrate when the acetate concentration becomes lower than said set value, and recovering said metabolite.

7. A method for producing a metabolite according to claim 6, wherein an inducer is added to produce the metabolite.

8. A method for producing a metabolite according to claim 7, wherein said inducer acts on a promoter in an expression vector which a recombinant bacterium bears.

9. A method for producing a metabolite according to claim 6, wherein said recombinant bacterium is a recombinant *Escherichia coli*.

10. A method for producing a metabolite according to claim 8, wherein the promoter in the expression vector which said recombinant bacterium bears is trp-promoter, lac-promoter, tac-promoter or $P_L$-promoter.

11. A method for producing a metabolite according to claim 10, wherein as said inducer, 3-$\beta$-indolylacrylic acid is used when the promoter is trp-promoter, and isopropyl-$\beta$-D-thiogalactoside is used when the promoter is lac-promoter or tac-promoter.

12. A method for producing a metabolite according to claim 6, wherein said metabolite is induced by using a tryptophan-free culture broth or a culture broth having a low tryptophan concentration when the bacterium is *Escherichia coli* containing trp-promoter or is induced by elevation of a temperature of the culture broth when recombinant bacterium is *Escherichia coli* bearing $P_L$-promoter.

13. A method for producing a metabolite according to claim 6, wherein said nutrient substrate is at least one selected form the group consisting of an amino acid, glucose and yeast extract.

14. A method for producing a metabolite according to claim 6, wherein said metabolite is a biologically active substance.

15. A method for producing a metabolite according to claim 6, wherein said metabolite is an enzyme.

* * * * *